(12) United States Patent
Rosenberg et al.

(10) Patent No.: US 7,582,309 B2
(45) Date of Patent: Sep. 1, 2009

(54) COHESIVE DEMINERALIZED BONE COMPOSITIONS

(75) Inventors: Aron D. Rosenberg, Brookline, MA (US); Laurent Gilles de Pelichy, Allston, MA (US)

(73) Assignee: Etex Corporation, Boston, MA (US)

( * ) Notice: Subject to any disclaimer, the term of this patent is extended or adjusted under 35 U.S.C. 154(b) by 56 days.

(21) Appl. No.: 10/298,112

(22) Filed: Nov. 15, 2002

(65) Prior Publication Data

US 2004/0097612 A1    May 20, 2004

(51) Int. Cl.
*A61F 2/28* (2006.01)

(52) U.S. Cl. .................. 424/423; 424/422; 623/16.11

(58) Field of Classification Search .................. None
See application file for complete search history.

(56) References Cited

U.S. PATENT DOCUMENTS

| | | | |
|---|---|---|---|
| 4,722,948 A | 2/1988 | Sanderson | 523/115 |
| 5,011,691 A * | 4/1991 | Oppermann et al. | 424/423 |
| 5,073,373 A | 12/1991 | O'Leary et al. | 424/422 |
| 5,284,655 A | 2/1994 | Bogdansky et al. | 424/422 |
| 5,290,558 A | 3/1994 | O'Leary et al. | 424/422 |
| 5,314,476 A | 5/1994 | Prewett et al. | 623/16 |
| 5,484,601 A | 1/1996 | O'Leary et al. | 424/422 |
| 5,507,813 A | 4/1996 | Dowd et al. | 623/16 |
| 5,510,396 A | 4/1996 | Prewett et al. | 523/113 |
| 5,676,146 A | 10/1997 | Scarborough | 128/654 |
| 5,707,962 A | 1/1998 | Chen et al. | 514/12 |
| 5,910,315 A | 6/1999 | Stevenson et al. | 424/422 |
| 6,030,635 A | 2/2000 | Gertzman et al. | 424/423 |
| 6,051,247 A | 4/2000 | Hench et al. | 424/423 |
| 6,123,731 A * | 9/2000 | Boyce et al. | 623/23.63 |
| 6,165,487 A | 12/2000 | Ashkar et al. | 424/426 |
| 6,180,606 B1 | 1/2001 | Chen et al. | 514/12 |
| 6,294,187 B1 | 9/2001 | Boyce et al. | 424/422 |
| 6,303,659 B2 | 10/2001 | Baxter et al. | 514/617 |
| 6,326,018 B1 | 12/2001 | Gertzman et al. | 424/423 |
| 6,340,477 B1 | 1/2002 | Anderson | 424/488 |
| 6,458,162 B1 * | 10/2002 | Koblish et al. | 623/23.51 |
| 2001/0014662 A1 | 8/2001 | Rueger et al. | 514/2 |
| 2001/0014667 A1 | 8/2001 | Chen et al. | 514/12 |
| 2001/0016646 A1 | 8/2001 | Rueger et al. | 530/840 |
| 2001/0018614 A1 | 8/2001 | Bianchi | 623/16.11 |
| 2001/0043940 A1 | 11/2001 | Boyce et al. | 424/423 |
| 2002/0018796 A1 | 2/2002 | Wironen | 424/423 |

FOREIGN PATENT DOCUMENTS

WO    WO 98/40113    3/1997

\* cited by examiner

*Primary Examiner*—Eric E. Silerman
(74) *Attorney, Agent, or Firm*—Clark & Elbing LLP

(57) ABSTRACT

Demineralized bone matrix fibers and a demineralized bone matrix composition are provided. The demineralized bone matrix fibers have an average fiber length in the range from about 250 μm to about 2 mm and an aspect ratio of greater than about 4. The demineralized bone matrix composition includes demineralized bone matrix fibers and a biocompatible liquid in an amount to produce a coherent, formable mass. The formable mass retains its cohesiveness when immersed in a liquid. Methods for making the demineralized bone matrix fibers and composition are also provided.

39 Claims, 5 Drawing Sheets

COHESIVE DEMINERALIZED BONE COMPOSITIONS

BACKGROUND OF THE INVENTION

1. Field of the Invention

The field of the present invention is bone repair and replacement. The invention relates to cohesive, formable, and injectable demineralized bone powder compositions, in particular, for use in implantation.

2. Description of the Relevant Art

Bone grafts are used to correct osseous defects that may be caused by trauma, pathological disease, surgical intervention or other situations. It is preferred to have the defect filler in the form of a stable, moldable putty to facilitate the placement of the bone growth medium into an osseous site, which is usually uneven in shape and depth. The medical specialist will take the putty on a spatula or other instrument and trowel it into the site or take it in his/her fingers and shape the bone inducing material into the proper configuration to fit or pack into the site being corrected.

The use of demineralized bone matrix (DBM) powder in the repair of bone defects has been a subject of investigation for some time. DBM is an osteogenic and osteoinductive material most commonly obtained from long bone chips demineralized by acid treatment. The acid treatment dissolves inorganic mineral components and acid-soluble proteins in the bone, leaving behind a collagen matrix as well as acid-insoluble proteins and growth factors. Among the remaining acid-insoluble proteins and growth factors are bone morphogenic proteins (BMPS) and transforming growth factors (TGFs). DBM is a desirable component of bone graft materials because it provides an osteoinductive matrix and exhibits osteoconductive potential, thereby promoting bone growth and healing (e.g. WO 00/45870). Moreover, DBM is fully resorbable, and bone graft materials containing organic DBM are highly biocompatible because it contains many of the components of natural bone. Advantageously, DBM costs less than many other available organic bone composition additives, such as isolated BMPs.

DBM is usually available in a lyophilized or freeze dried and sterile form to provide for extended shelf life. The bone in this form is usually very coarse and dry and is, therefore, not conducive to surgical manipulation.

U.S. Pat. No. 5,073,373 discloses a deformable, shape-sustaining osteogenic composition, in which DBM particles are dispersed within a liquid polyhydroxy carrier, such as glycerol. The vast majority of the DBM particles possess random, irregular geometries with an average median length to median thickness ratio of from about 1:1 to about 3:1. The combination of the glycerol's high water solubility and reduced viscosity causes the composition to be "runny" and to flow away from the site almost immediately after placement, thus preventing the proper retention of the composition at the implant site (U.S. Pat. No. 6,030,635).

Bone particles having a median length to median thickness ratio of at least about 10:1 have been used in osteogenic compositions (U.S. Pat. Nos. 5,314,476, 5,510,396 and 5,507,813). These elongated particles have a median length of from about 2 mm to at least about 400 mm and a median thickness from about 0.05 mm to about 2 mm. The DBM fibers are commercially available as a preformed fiber sheet, matrix, or workable putty from Osteotech Corporation (Shrewsbury, N.J.) under the trade names Grafton® DBM Putty, Grafton® DBM Flex, and Grafton® DBM Matrix. Although the use of long DBM fibers improves both the bulk viscosity and the handling characteristics of a glycerol mixture, U.S. Pat. No. 5,510,396 indicates the mixture still lacks cohesiveness. The mixture's rapid dissipation rate due to the miscibility of the glycerol carrier in aqueous environments remains a problem. The larger DBM particles may also retard the development of new bone by the patient because the large particles do not pack as well as the smaller, grainy particles of bone. This leaves more open space in the mixture and lengthens the time required to grow new bone and properly fill the defect.

In order to address the lack of cohesiveness of DBM at implant sites, the use of binders, such as carboxymethyl cellulose, or the use of high molecular weight hydrogels or other polymers as carrier vehicles has been reported (U.S. Pat. Nos. 6,030,635 and 6,340,477). However, these binders can negatively affect the biocompatibility and osteoinductivity of the DBM composition. Furthermore, these binders provide cohesiveness to the composition only prior to its implantation; following implantation, these binders are eroded or dissolved from the implant site and, consequently, the implant does not retain its shape in vivo.

The ability of a DBM composition to retain its shape during and after implantation is desirable so that it is able to resist erosion when used as an implant, for example, at an osseous or semi-osseous defect site.

SUMMARY OF THE INVENTION

In one aspect of the present invention, a demineralized bone matrix (DBM) composition is provided that retains its shape ("cohesiveness") before, during and after implantation. The present inventors have surprisingly discovered that, when mixed with a biocompatible liquid, short DBM fibers form a coherent, formable mass, which retains its cohesiveness even when the mass is subjected to large volumes of fluid, e.g., water, saline or bodily fluids. The shape and mass of the composition is retained without the use of binders or high viscosity carrier vehicles, as is required in prior art compositions.

In one aspect of the present invention, the DBM composition includes DBM fibers, having an average fiber length in the range from about 250 µm to about 2 mm and an aspect ratio of greater than about 4, and a biocompatible liquid in an amount to produce a coherent, formable mass. The formable mass retains its cohesiveness when immersed in a liquid.

In one or more embodiments, the DBM fibers have an average thickness in the range from about 50 µm to about 250 µm.

In one or more embodiments, the aspect ratio is greater than about 10, or the aspect ratio is in a range from about 10 to about 50.

In one or more embodiments, the DBM fibers have an average width to average thickness ratio of less than about 5.

The DBM composition may optionally contain DBM particles having an aspect ratio of less than about 3.

The DBM composition may optionally contain an osteoinductive additive to enhance bone ingrowth and remodeling.

The DBM composition may optionally contain an osteoconductive additive to promote the transport of cells, e.g. osteoclasts and osteoblasts, within the composition.

The DBM composition may optionally contain an additive that modifies the composition's handling characteristics; however, such an additive is not required to maintain a minimal acceptable level of cohesiveness. In one or more embodiments, this additive at least partially coats the DBM fibers.

In one or more embodiments, the relative amounts of the DBM fibers and biocompatible liquid range from 1:10 to 10:1, or 1:4 or 4:1, or about 1:1.

In one or more embodiments, the DBM fibers are obtained from cortical autogenic, cortical allogenic, cortical xenogeneic, cancellous autogenic, cancellous allogenic, cancellous xenogeneic, corticocancellous autogenic, corticocancellous allogenic, or corticocancellous xenogeneic bone.

In one or more embodiments, the DBM composition is injectable through an 18-gauge needle.

In another aspect of the invention, the DBM composition includes a dry component, comprising DBM fibers having an average fiber length in the range from about 250 µm to about 2 mm and an average aspect ratio of greater than about 4, and a biocompatible fluid in an amount to provide a coherent formable mass. The DBM fibers are present in an amount greater than 40 wt % of said dry component. The formable mass retains its cohesiveness when immersed in a liquid.

In another aspect of the invention, a collection of DBM fibers is provided, of which at least about 25 wt % have an average fiber length in the range from about 250 µm to about 2 mm and an aspect ratio of greater than about 4.

In another aspect of the invention, a preformed DBM article having a predetermined shape is provided, wherein the preformed article comprises DBM fibers having an average fiber length in the range from about 250 µm to about 2 mm and an aspect ratio of greater than about 4 and a biocompatible liquid in an amount to produce a coherent, formable mass. The formable mass retains its cohesiveness when immersed in a liquid.

In one or more embodiments, the preformed DBM article has a density in the range of about 0.3 g/cc to about 0.7 g/cc.

In one or more embodiments, the preformed DBM article has a compression strength greater than about 10 MPa.

In another aspect of the invention, a method for making a DBM composition is provided, wherein DBM fibers having an average fiber length in the range from about 250 µm to about 2 mm and an aspect ratio of greater than about 4 and a biocompatible liquid are combined to produce a coherent, formable mass. The formable mass retains its cohesiveness when immersed in a liquid.

In still another aspect of the invention, a method for making a DBM fiber is provided, wherein bones are shaved to obtain bone shavings such that osteons are aligned within the plane of the bone shavings; the bone shavings are fragmented to obtain needle-like bone fragments; and the bone is demineralized before, during, or after fragmentation.

In yet another aspect of the invention, a method of making a preformed DBM article is provided, wherein DBM fibers having an average fiber length in the range from about 250 µm to about 2 mm and an aspect ratio of greater than about 4 and a biocompatible liquid are combined to produce a coherent, formable mass; the mass is formed into a preformed article having the predetermined shape; and the preformed article is dried.

In one or more embodiments, the preformed article is lyophilized. In one or more embodiments, the lyophilized preformed article has a density of about 0.3 g/cc.

In one or more embodiments, the preformed article is oven dried. In one or more embodiments, the oven dried preformed article has a density of about 0.7 g/cc.

The term "about" is used herein to mean a value that is ±10% of the recited value.

"Cohesiveness" is used herein to mean the ability of DBM, when mixed with a biocompatible fluid, to form a malleable or flowable mass and to maintain its shape without loss of mass. A mixture is deemed cohesive if greater than 90% of its initial mass and volume are retained within its initial shape dimension in an aqueous environment for at least 10 minutes.

The expression "average length to average thickness ratio" as applied to the DBM fibers of the present invention means the ratio of the longest dimension of the fiber (average length) to its shortest dimension (average thickness). This is also referred to as the "aspect ratio" of the fiber.

BRIEF DESCRIPTION OF THE DRAWINGS

The invention is described with reference to the following figures, which are presented for the purpose of illustration only and which are not intended to be limiting of the invention.

DETAILED DESCRIPTION OF THE INVENTION

Demineralized bone matrix (DBM) fibers having an average length in the range from about 250 µm to about 2 mm and an average length to average thickness ratio ("aspect ratio") greater than about 4 and less than about 100 are provided. In one or more embodiments, the DBM fibers have a median thickness in the range from about 50 µm to about 250 µm. In one or more embodiments, the DBM fibers have an aspect ratio of greater than about 10, or in the range from about 10 to about 50. In at least some embodiments, the DBM fibers have an average width to average thickness ratio of less than about 5.

Figure 1:
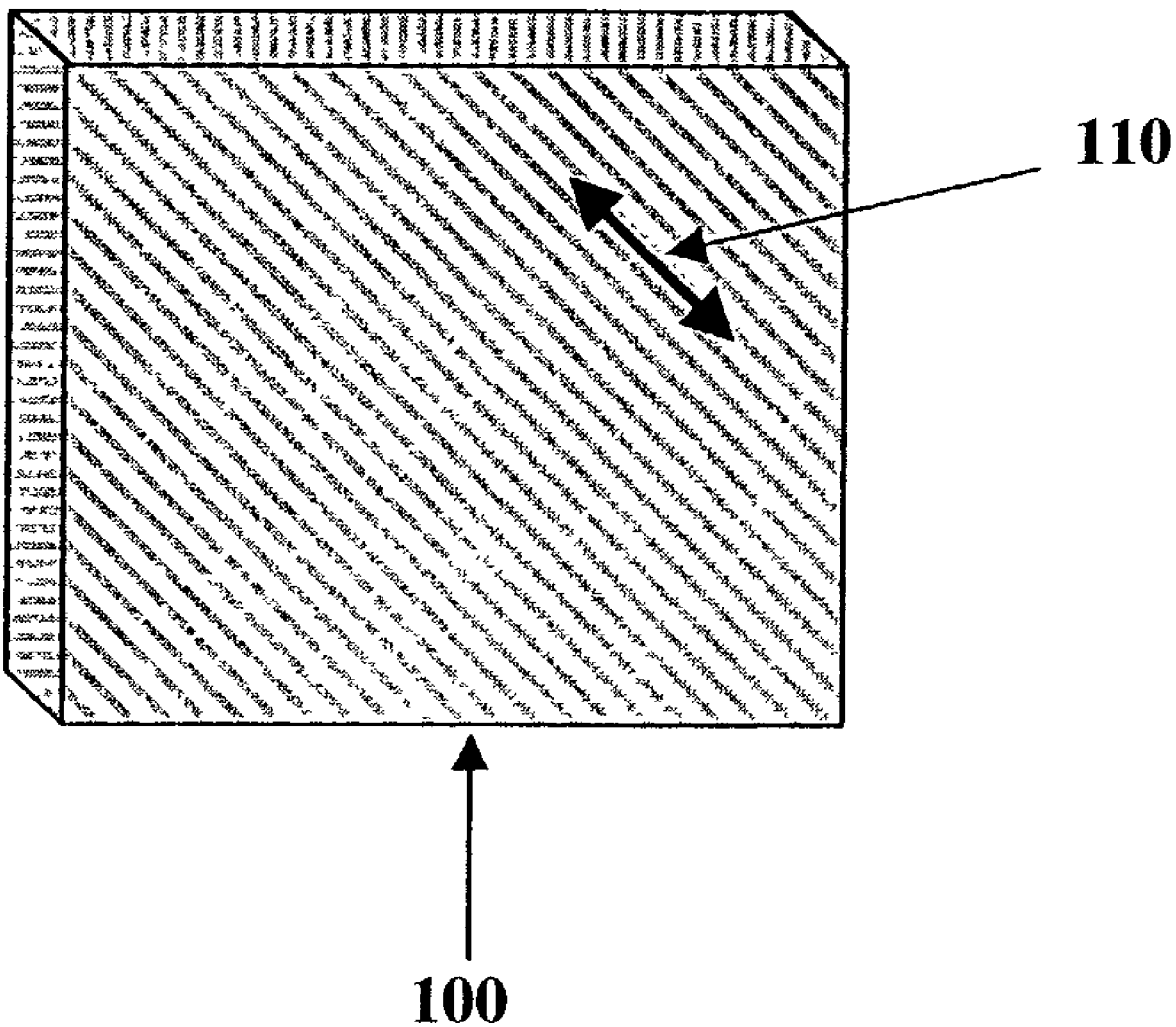
FIG. 1 is a schematic illustration of characteristic bone shaving or plate with osteons aligned within the plane of the shaving.
Figure 2:
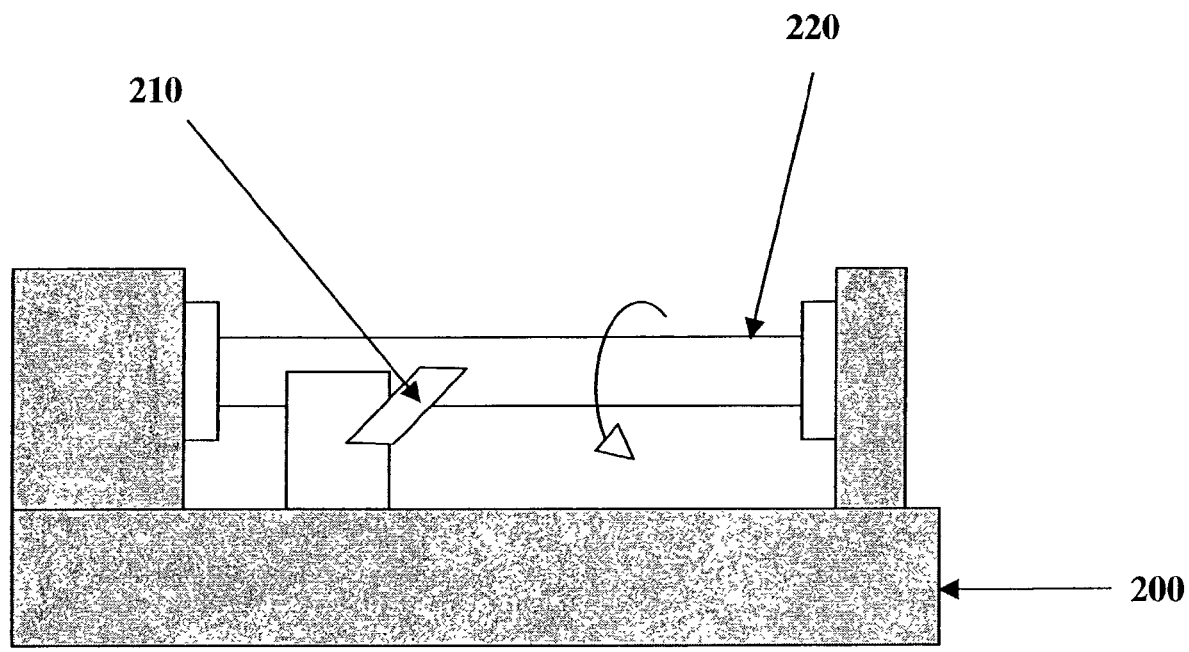
FIG. 2 is a schematic illustration of a bone shaving apparatus used in the practice of one or more embodiments of the present invention.
Figure 3:
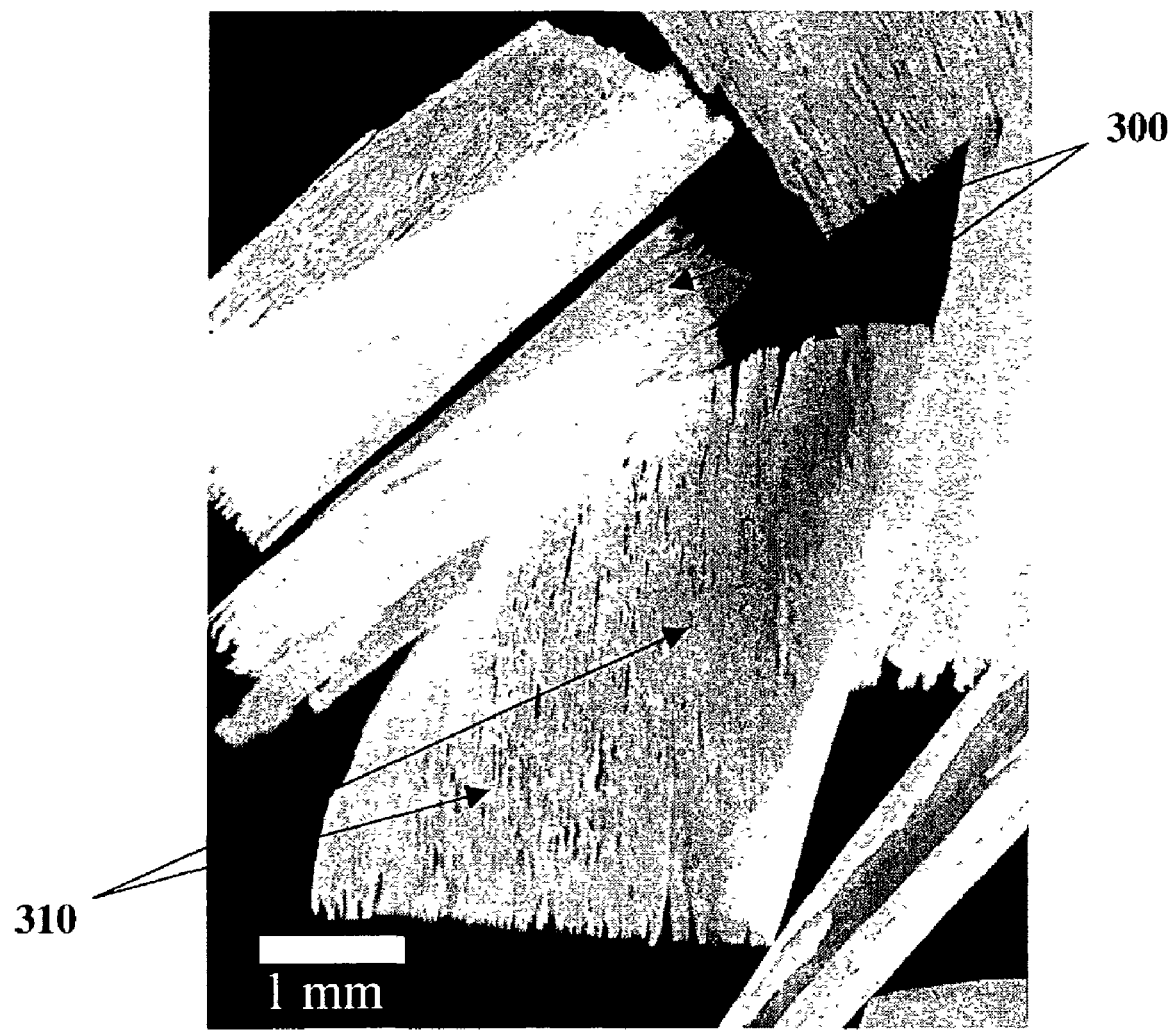
FIG. 3 is a photomicrograph of cortical bone shavings prior to demineralization according to at least some embodiments of the present invention.

Natural bone includes compact, noncancelous bone containing parallel and laminar osteons. To prepare short fiber DBM according to one or more embodiments of the present invention, cortical bone, either defatted or undefatted, is shaved into thin (<250 µm) shavings or plates 100 such that the natural bone lamellae, or osteons 110, are aligned within the plane of the shavings or plates (FIG. 1). Cortical bone osteons are naturally aligned along the bone length such that cortical bone is particularly suited for such a shaving process. As shown in FIG. 2, thin bone shavings are derived by turning long bone 220 in a bone lathe 200, which contains a cutting tool 210. The resultant bone shavings or plates typically have a thickness between about 50 µm and about 250 µm and a width between about 2 mm and about 30 mm. Exemplary thin bone shavings 300 are shown in the photomicrograph of FIG. 3. The linear array of osteons 310 is clearly visible. Short fiber DBM according to one or more embodiments of the present invention may be prepared from cortical, cancellous or corticocancellous bone derived from autogenic, allogenic or xenogeneic sources. Corticocancellous and cancellous bone, because they are less dense and exhibit a lesser degree of osteon alignment than cortical bone, cannot be subjected to the shaving procedure described above but may be cut into short fibers using conventional methods known to those of skill in the art.

Following shaving, the bone shavings or plates are subjected to demineralization so as to reduce their inorganic content to a very low level. The bone fragments may be defatted prior to demineralization. During demineralization appropriate agitation is applied to the solution to cause delamination of the bone fibers, resulting in the formation of fine rope-like DBM fibers. The fibers are then rinsed with water and/or an appropriate buffer to remove the solubalized mineral and excess acid. The resultant fibers are of low inorganic content, e.g. typically not more than 1% by weight of residual calcium. The fibers are then dried by traditional methods, for example, by oven drying or lyophilization. In one or more embodiments, the fibers are combed to reduce entanglement using standard fiber combing techniques known to those of skill in the art.

Figure 4:
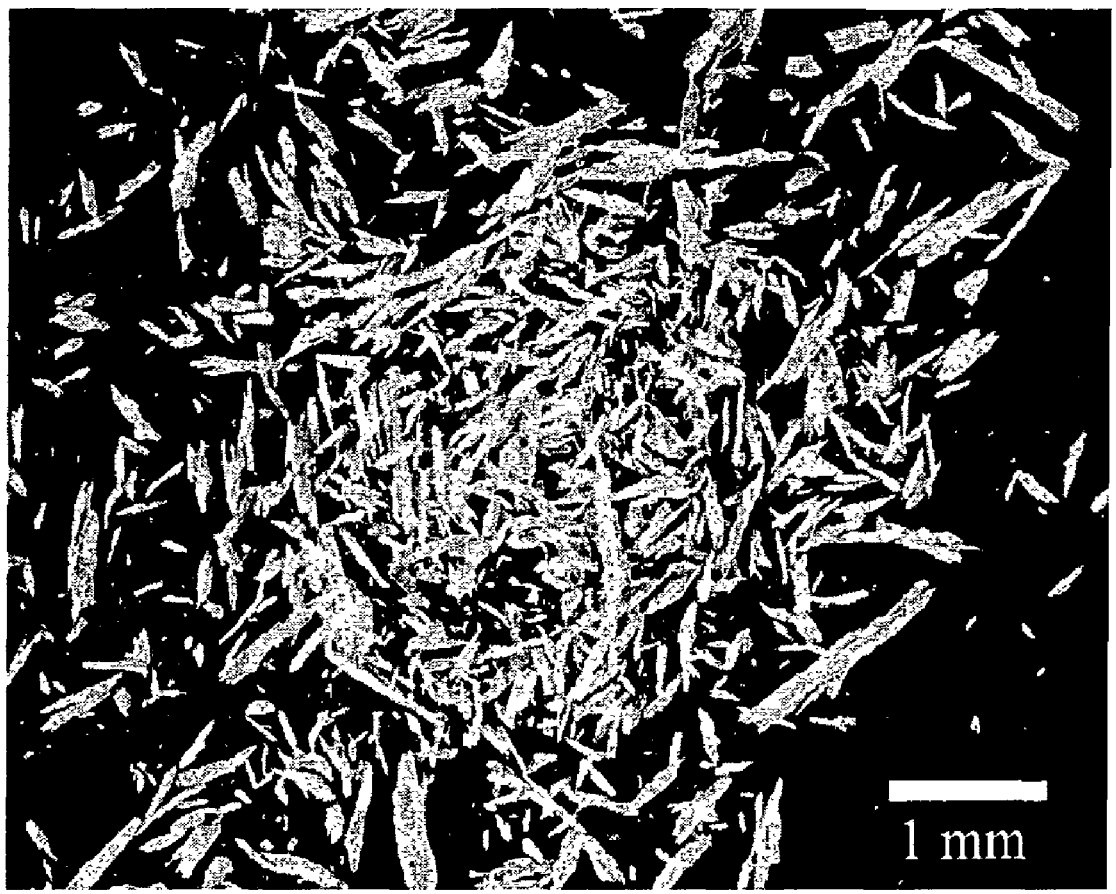
FIG. 4 is a photomicrograph of cortical bone needles prior to demineralization according to at least some embodiments of the present invention.

In one or more embodiments of the present invention, bone needles are formed prior to demineralization by directly shaving or machining needles or mechanically breaking down bone shavings and plates. Bone shavings and plates may be stirred in an aqueous or non-aqueous solution or dry milled to form needles. Exemplary short, high aspect ratio bone needles are shown in FIG. 4. The needle structure promotes the formation of high aspect ratio DBM fibers and further increases the surface area of the shaved bone for more effective and efficient demineralization.

Demineralization occurs rapidly due to the high surface area of the thin bone shavings or needles. Compared to conventional demineralization processes using bone chips or larger fibers, demineralization is successfully accomplished using less aggressive acid conditions and/or shorter reaction times. For example, short fibers according to one or more embodiments of the present invention are fully demineralized in a 0.5 M HCl solution after 1 hour as compared to a more conventional process in which larger bone pieces are demineralized in a 0.5 M HCl solution after 3 hours. These milder demineralization conditions cause less damage to the organic component of the DBM. In particular, sensitive proteins and osteogenic factors may retain a higher level of activity after processing according to at least some embodiments of the present invention. Higher levels of osteoinductivity and bone ingrowth are, therefore, expected with these DBM fibers as compared to conventionally-processed DBM particles.

Figure 5:
FIG. 5 is a photomicrograph of DBM fibers according to at least some embodiments of the present invention.

The resultant DBM fibers form fine, rope-like fibers as shown in FIG. 5. The fibers are of irregular shape, having linear, serpentine, hooked or curved shapes. Due to the variety and complexity of fiber shapes, the fibers often interlock. Although not bound by any particular theory or mode of operation, it is believed that the ability of the short fiber DBM of the present invention to interlock is advantageous to the formation of coherent DBM compositions. As previously mentioned, the fibers may be combed using standard fiber combing techniques known in the art to reduce entanglement.

To prepare a DBM composition according to one or more embodiments of the present invention, a quantity of short DBM fibers prepared as described above is combined with water or any other appropriate, biocompatible liquid to form a smooth, flowable, cohesive paste. The resultant composition may be molded or injected into any desired shape and retains its shape, even when submersed in water, saline, or other aqueous solution. An additional benefit of the short DBM fibers is that the resultant paste is injectable through an 18-gauge needle. In contrast, paste compositions using DBM fibers having the dimensions of the Grafton® DBM fibers or standard irregular particle size DBM cannot be injected through an 18-gauge needle.

The liquid may be any biocompatible liquid, including water, saline solution, buffered solutions, serum, bone marrow aspirant, blood, platelet-rich plasma and the like and mixtures thereof. Some biocompatible liquids suitable for use with the short DBM fibers, such as serum, bone marrow aspirant and blood, additionally contain osteoinductive factors that will promote bone growth at the site to which the composition is applied.

The ability of the short fiber DBM compositions of the present invention to form a cohesive, flowable mixture when combined with only water or saline distinguishes the inventive compositions from previous DBM compositions, which require viscous carrier liquids (e.g. glycerol, gel, gelatin, hyaluronic acid, or hydrogel polymers) or even binders to form a cohesive material. Note that, while the short fiber DBM compositions of the present invention may be formed using aqueous solutions, the compositions are not limited to the use of such aqueous solutions. The short fiber DBM of the present invention may be used with any biocompatible liquid. Other exemplary biocompatible liquids include but are not limited to liquid polyhydroxy compounds, liquid polyhydroxy compound derivatives, liquid solutions of solid polyhydroxy compounds, liquid solutions of solid polyhydroxy compound derivatives, liquid polyhydroxy compound esters, liquid solutions of a solid polyhydroxy compound esters, glycerol, glycerol monoester, glycerol diester, monosaccharides, monosaccharide derivatives, disaccharides, disaccharide derivatives, oligosaccharides, oligosaccharide derivatives, polysaccharides, polysaccharide derivatives, glucose, sucrose, fructose, dextrose, liquid solutions of fatty acid monoesters, liquid solutions of glycerol monolaurate, monoacetin, diacetin, sodium hyaluronate, chitosan, N,O-carboxymethylchitosan, gelatin and solutions of the foregoing and are described in, among others, U.S. Pat. Nos. 5,073,373, 5,284,655, 5,290,558, 5,314,476, 5,510,396, 6,030,635, 6,051,247 and WO 98/40113, which are hereby incorporated by reference.

The biocompatible liquid is used in any amount sufficient to provide a malleable or flowable mixture. In exemplary formulations, the ratio of short fiber DBM to carrier liquid ranges from about 1:19 to 19:1 wt/wt, or about 1:10 to 10:1 wt/wt, or about 1:4 to 4:1 wt/wt, or about 2:1 to 1:2 wt/wt, or about 1:1 wt/wt, depending on the desired Theological properties of the composition.

Additional components may optionally be included in the short fiber DBM composition. In one or more embodiments, the short fiber DBM composition may additionally include particulate DBM. The particulate DBM may be used as an extender of the short fiber DBM composition. Particulate DBM is easier to obtain than short fiber DBM and, to some extent, results from the processing of bone as previously described. Particulate DBM suitable for use with the short fiber DBM has an aspect ratio less than about 3 and is used in quantities such that the composition maintains the advantages afforded by the short fiber DBM. DBM particles can range from 0-75 wt %, and more preferably 0-50 wt %.

In one or more embodiments, an osteoinductive component is included in the short fiber DBM composition to further enhance the osteoinductivity of the paste. Thus, the DBM fibers and biocompatible liquid may be mixed with bone marrow aspirant, blood, blood products, particulate DBM, synthetic or naturally-derived BMPs, or other growth factors, such as TGF or osteogenic proteins, or protein-rich plasma (PRP). Alternatively, as previously mentioned, the biocompatible liquid itself may be a source of osteoinductive components. The amount of osteoconductive component can vary greatly. When the biocompatible liquid is osteoconductive, the osteoconductive component may be as much as 90% by weight or 50% by weight or 10% by weight of the paste. In some embodiments, the osteoconductive component is a protein present in small amounts, e.g. less than 5 wt % of the paste.

DBM fibers are naturally osteoconductive, as cells, e.g. osteoclasts and osteoblasts, can move along the length of the fiber to gain access to the composite interior. The interlocking fiber network provides a continuous pathway for improved cellular access over particulate DBM. Due to the smaller fiber dimensions of the DBM of the present invention, the DBM fibers can pack more densely than the long fibers of the prior art; an improvement in osteoconductivity is, therefore, expected.

In one or more embodiments, an additional osteoconductive component is included in the short fiber DBM composition to further promote the transport of cells within the composition. Exemplary osteoconductive compounds include calcium phosphates, collagen, collagen-derivatives, calcium sulfate, particulate DBM, naturally-derived allogenic bone mineral or naturally-derived autogenic bone mineral. In exemplary embodiments, osteoconductive compounds are added to the composition in an amount ranging from about 20 to about 80 wt %, or about 25 to about 65 wt %, of the total weight of dry component.

In one or more embodiments, short fiber DBM is combined with one or more inorganic calcium phosphates that mimic the chemical composition of naturally-occurring bone mineral. These inorganic compositions are osteoconductive, serve as carriers for the osteogenic materials and may be used to provide strength and/or rigidity to the bone grafts. Calcium phosphate ceramic compositions, such as those including hydroxyapatite and/or tricalcium phosphate (e.g. WO 01/08714 and WO 00/45870, which are incorporated herein by reference) and resorbable calcium phosphate compositions, such as those including amorphous calcium phosphate or poorly crystalline apatitic (PCA) calcium phosphate (e.g. U.S. Pat. No. 6,027,742, which is incorporated herein by reference), may be used. These resorbable calcium phosphate compositions are capable of remodeling into naturally-occurring bone mineral and, therefore, lack the problems associated with the implantation of permanent foreign bodies. In one or more embodiments, an osteogenic additive includes a nanocrystalline calcium phosphate powder prepared from the high energy milling of more crystalline calcium phosphates. The high energy milled calcium phosphates are highly reactive and, upon combination with an appropriate physiologically acceptable fluid, are capable of self-setting into an apatitic calcium phosphate that closely resembles the mineral component of naturally occurring bone. Further detail is provided in copending U.S. application Ser. No. 10/222,670, which is incorporated herein by reference.

Thus, according to one or more embodiments of the instant invention, the short fiber DBM is provided in a calcium phosphate powder. The calcium phosphate powder may be composed of a single calcium phosphate, e.g. an amorphous calcium phosphate, or two or more intimately mixed calcium phosphate sources, at least one of which is an amorphous calcium phosphate. As used herein, "amorphous" describes calcium phosphate particles having no or only short range crystallographic order, i.e. crystallographic order over less than 100 nm. Amorphous calcium phosphate has a broad, diffuse X-ray diffraction pattern, is homogenous when measured on an Angstrom scale and is a gel-like material formed by rapid precipitation from a solution containing calcium and phosphate ion sources. The rapid precipitation creates numerous defects in the calcium phosphate nuclei. Under physiological conditions, amorphous calcium phosphate has a high solubility, high formation rate and high rate of conversion to PCA calcium phosphate.

Amorphous calcium phosphate has a Ca/P ratio in the range of about 1.1 to about 1.9. In at least some embodiments of the instant invention, the amorphous calcium phosphate has a Ca/P ratio of less than about 1.5. In particular embodiments, the Ca/P ratio is between about 1.35 and about 1.49. The Ca/P ratio of the amorphous calcium phosphate may be modified by the introduction of additional ions into the calcium and phosphate ion-containing solution. Non-limiting examples of such additional ions include $CO_3^{2-}$, $Mg^{2+}$, $P_2O_7^{4-}$, nitrate, nitrite or acetate ions. The preparation and characterization of amorphous calcium phosphates are described further in U.S. Pat. Nos. 5,650,176 and 6,214,368, which are incorporated herein by reference.

An additional calcium phosphate source may be included in the calcium phosphate powder. Appropriate additional calcium phosphate sources for use in the instant invention include acidic, basic and neutral calcium phosphates having a stoichiometry such that they produce apatitic calcium phosphates upon reaction with amorphous calcium phosphate. Non-limiting examples of suitable acidic calcium phosphates include calcium metaphosphate, dicalcium phosphate dihydrate, heptacalcium phosphate, tricalcium phosphate, calcium pyrophosphate dihydrate, poorly crystalline hydroxyapatite, calcium pyrophosphate and octacalcium phosphate. Exemplary basic calcium phosphates include additional amorphous calcium phosphates. In particular embodiments, the second calcium phosphate source is dicalcium phosphate dihydrate (DCPD).

When using two or more calcium phosphate sources, the calcium sources should be selected such that they will produce a calcium phosphate powder having a desired overall Ca/P ratio. The first and second calcium phosphates are used in proportions ranging from 1:10 to 10:1, or 1:5 to 5:1, or about 1:1 of the first and second calcium phosphate, respectively. Because the reaction forming PCA calcium phosphate proceeds substantially to completion, the Ca/P ratio of the calcium phosphate sources should be equivalent to that of the product. PCA calcium phosphate has a Ca/P ratio between about 1.1 and about 1.9. Thus, according to at least some embodiments of the instant invention, the unreacted calcium phosphate sources should have a Ca/P ratio between about 1.1 and about 1.9. In at least some embodiments, the Ca/P ratio may range from 1.1 to 1.7 and may be that of the desired product calcium phosphate, i.e. poorly crystalline apatitic (PCA) calcium phosphate having a Ca/P ratio of less than 1.67.

In at least some embodiments of the invention, the calcium phosphate is present in the composition in a significant amount. Thus, in some embodiments of the invention, the calcium phosphate is present in an amount greater than or equal to about 20 wt % of the dry component. In particular embodiments, the calcium phosphate is present in an amount greater than or equal to about 40 wt % of the dry component.

In one or more embodiments, the calcium phosphate powder forms a self-setting calcium phosphate cement when combined with an appropriate physiologically acceptable fluid.

In one or more embodiments, an additive is included in the DBM composition to further modify the handling characteristics of the composition, such as viscosity and moldability. The additive may be a biocompatible polymer, such as a water-soluble cellulosic (e.g. carboxymethyl cellulose), or a natural polymer, such as gelatin. The additive may be added to either the dry DBM component or the liquid component.

The additive may be used to at least partially coat the DBM fibers prior to combining them with the liquid carrier. Non-limiting examples of additives suitable for use in the DBM composition include gelatin, carboxymethyl cellulose, hydroxypropyl methylcellulose, methylcellulose, hydroxyethyl cellulose, other cellulose derivatives, alginate, hyaluronic acid, sodium salts, polyvinyl pyrrolidones, polyvinyl alcohol, arabic gum, guar gum, xantham gum, chitosans, and poloxamers.

The amount of short fiber DBM that is incorporated in the composition may vary widely, with amounts ranging from about 5 to about 100 wt % of the dry component of the composition, or about 20 to about 80 wt % of the dry component of the composition, or more than about 40 wt % of the dry component of the composition. The balance of the dry component is comprised of the optional components, if any. In at least some embodiments, the short fiber DBM constitutes about 5 to about 90% of the volume of the total composition.

The DBM composition of the present invention may be provided in the form of a kit to facilitate on-site preparation. The kit may include separate packages of the dry (preferably lyophilized), sterile DBM fiber and biocompatible liquid. Optional ingredients may be included with either or both packets, depending upon their compatibility with the DBM component or the biocompatible liquid. The contents of the separate containers may be brought together for mixing immediately before use. Alternatively, the DBM composition may be prepared well in advance and stored under sterile conditions until required for use.

As previously mentioned, the DBM composition of the present invention is prepared by mixing desired quantities of short fiber DBM, biocompatible liquid and optional additive, if any, in any suitable sequence of mixture operations or all at once. Thus, the short fiber DBM may be mixed with optional ingredients or the optional ingredients may be added to the biocompatible liquid followed by addition of the DBM component. Variations of these and other sequences are contemplated according to the invention.

After mixing, the composition is delivered to an implant site using methods appropriate to the implant site. In some embodiments, the composition is injected into the implant site. In some embodiments, the composition is formed into the desired shape and packed into the implant site.

In some embodiments, the DBM composition may be prepared as a high or low density preformed device of any desired shape. After mixing of the short fiber DBM, biocompatible liquid, and any optional components, the composition may be formed into the desired shape by molding, extrusion, injection molding, pressure molding, casting, or any other suitable method known to those of skill in the art. The preformed device is lyophilized or vacuum dried. The liquid volume and drying technique may be controlled so as to modify the pore volume and pore size of the resulting preformed device. Thus, lyophilization will prevent shrinkage of the composition and maintain the voids filled with the biocompatible liquid. According to this method, low density, high porosity preformed devices may be prepared having a density as low as about 0.3 g/cc. In contrast, vacuum drying and the addition of pressure will shrink the composition and collapse the voids filled with the biocompatible liquid. According to this method, high density, high strength preformed devices may be prepared having a density as high as about 0.7 g/cc and a compression strength greater than about 10 MPa.

The following examples further illustrate certain embodiments of the present invention and are not to be considered limiting of the invention.

EXAMPLE 1

Formation of Short Fiber Demineralized Bone Matrix

This Example describes the preparation of short fiber DBM.

Long bones were cleaned to remove all connective tissue. The end plates were removed to isolate the cortical bone component of the long bone, and the marrow was removed. The hollow long bones were washed in alcohol to further clean and remove fat. The bones were then turned on a lathe. Shavings were made by pressing a straight edged silicon carbide cutting tool into the surface of the bone, as illustrated in FIG. 2. The cutting tool advances along the length of the bone to provide a length of bone shaving. The rate of rotation of the bone in concert with the rate of motion of the cutting tool can be controlled by those familiar with the process so as to control the rate of material removal. Shavings of thickness varying between 50 μm and 250 μm, widths between 2 mm and 10 mm and random length were obtained by this process (FIG. 3). These shavings were then washed in ether to remove the remaining fats. Demineralization was performed by stirring the shavings in 0.5 molar hydrochloric acid (HCl) for 1 hour. After demineralization, the fibers were rinsed in deionized water until the excess acid was removed. The fibers were then dried by rinsing in alcohol and ether and allowing the ether to evaporate. Average fiber length was distributed randomly between about 250 μm and about 2 mm, and average fiber thickness was between about 50 μm and about 250 μm. This process also resulted in a small but significant fraction (<20% by weight) of fine particles. Most of these particles are approximately the same size as the DBM fibers, although some are larger.

EXAMPLE 2

Preparation of a Short Fiber DBM Composition

This example describes the preparation of a short fiber DBM composition and evaluates its cohesiveness.

The cohesive properties of a sample prepared as described above were compared to those of a sample prepared from Grafton® DBM fibers. 0.5 cc of Grafton® DBM Putty, which is supplied as a premixture of Grafton® DBM Fibers in glycerol, were mixed according to provided instructions to form a malleable paste. The paste was formed into a ball about 0.5 cm in diameter, and the ball was dropped into a beaker of water. The mass immediately broke up and dispersed into individual component fibers, losing all physical integrity. Thus, 100% of the sample mass was dispersed from the initial shape dimension into solution within 10 minutes.

A 0.25 gram sample of short fiber DBM prepared as described in Example 1 was combined with 0.5 cc of distilled water to form a malleable paste, which was also formed into a ball about 0.5 cm in diameter. The short fiber DBM sample was dropped into water. The ball retained its initial shape, without significant observable distortion, swelling or mass loss, for at least 10 minutes. The sample was removed from the water and the water was filtered to determine the extent of fiber loss from the sample upon immersion. No measurable amount of fiber loss was observed.

EXAMPLE 3

Preparation of Short Fiber DBM Paste

This example describes the preparation of an implant of a short fiber DBM paste.

1.0 g of short fiber DBM, prepared as described in Example 1, was combined with 1.6 cc of saline to form a paste. 0.10 cc of the paste was extruded through a 1 cc Becton Dickinson slip tip syringe, having a cut-off tip, to form a 0.1 cc paste cylinder.

EXAMPLE 4

Preparation of Short Fiber DBM—Calcium Phosphate Paste

This example describes the preparation of an implant of a short fiber DBM—calcium phosphate paste. The paste may optionally contain an additive.

0.6 g of short fiber DBM, prepared as described in Example 1, was combined in a mixing jar with 0.3 g of a nanocrystalline calcium phosphate powder comprising amorphous calcium phosphate (ACP) and dicalcium phosphate dihydrate (DCPD). The nanocrystalline calcium phosphate powder was prepared as follows.

Preparation of ACP: A solution of 150 g of disodium hydrogen phosphate heptahydrate ($Na_2HPO_4.7H_2O$) in 2167 mL distilled water was prepared and stirred. 83.3 g NaOH, 50 g $NaHCO_3$, and 3.3 g sodium pyrophosphate decahydrate ($Na_4P_2O_7.10H_2O$) were added sequentially to the solution to form solution 1. A solution of 31.2 g calcium nitrate tetrahydrate ($Ca(NO_3)_2.4H_2O$) in 833 mL distilled water was prepared and stirred. 1.7 g magnesium chloride hexahydrate ($MgCl_2.6H_2O$) was added to the solution to form solution 2. Solution 2 was poured quickly into solution 1 at room temperature and stirred for 1 minute. Precipitation was immediate and substantially complete. The pH of the suspension was 13±0.5, which was maintained to avoid conversion of the precipitate to an apatite or other more crystalline calcium phosphate. The precipitate was promptly separated from its mother solution using a basket centrifugal filtration and washed with about 15 L distilled water. Completion of washing was confirmed by the last wash ionic conductivity <300 µs. A gel cake of about 500 g amorphous calcium phosphate was obtained. The wet cake was immediately lyophilized to preserve the amorphous structure during drying, which removed about 80% of the water. About 100 g of the lyophilized powder was calcinated at 450° C. for 1 hour. The Ca/P ratio of the product was less than 1.5, and typically 1.35-1.49.

Preparation of DCPD: DCPD was prepared at room temperature by the rapid addition of a solution of calcium nitrite tetrahydrate (17.1 g in 250 mL distilled water) into a solution of diammonium hydrogen phosphate (10 g in 500 mL distilled water at a pH of 4.6-4.8) with constant stirring. Immediately thereafter, the sample was filtered using filter paper (0.05 sq. ft) with medium filter speed and a vacuum pressure of about $10^{-2}$ torr. The material formed a thin cake, which was washed with about 2 liters of distilled water and then dried at room temperature for 24-72 hours. A highly crystalline DCPD was obtained.

100 g of crystalline DCPD and amorphous calcium phosphate (1:1 by weight) were combined and the mixed powder was ball milled in a Attritor Model 01HD (50 g powder, 3 h, 100 rpm).

Optionally, Hercules 7HFPH carboxymethyl cellulose (0.1 g) was added to the nanocrystalline calcium phosphate powder. 1 cc saline was added per gram dry component to form a paste, which sets within 10 minutes at 37° C.

EXAMPLE 5

Preparation of Short Fiber DBM Preformed Device

This Example describes the preparation of a short fiber DBM preformed device in the shape of a cylinder.

A short fiber DBM paste cylinder was prepared as described in Example 3. The paste cylinder was then dried in a vacuum oven for four hours at 35° C. to produce a preformed device in the shape of a cylinder. The device had a density of about 0.6 g/cc.

EXAMPLE 6

Preparation of Particulate DBM

This Example describes the preparation of particulate DBM.

Diaphyses of sheep long bones, primarily fibulas and tibias, were isolated using a sagital saw. Using a scalpel, the periosteum and connective tissue were removed from the surface of the bone. The bones were split, and the marrow was removed.

The bones were then crushed into approximately 5 mm×5 mm×15 mm pieces. These bone pieces were cleaned and defatted by consecutive rinsing in 4° C. deionized water, 100% absolute ethanol, and anhydrous ether. The dry, defatted bone chips were ground under cryogenic conditions in a SPEX Freezermill 6800. The resulting bone powder was sieved to between about 125 µm and about 850 µm using stainless steel sieves.

The sieved bone powder was demineralized by stirring in 0.50 normal hydrochloric acid at room temperature for 3 hours. The DBM powder was then collected and rinsed with deionized water, 100% absolute ethanol, and anhydrous ether.

EXAMPLE 7

Implantation of Short Fiber DBM Compositions

Assessment of ectopic bone formation after implantation in intramuscular or subcutaneous pockets within an athymic rat is the current standard for characterizing osteoinductive materials. This Example describes the use of this model to assess short fiber DBM compositions and to compare those compositions to other DBM formulations.

Six to seven week old male athymic rats (*Rattus norvegicus*, Crl:NIH-rnu nudes, Charles River Laboratories) were housed and maintained in an isolator or microisolator equivalent under conditions recommended in the "Guide for the Care and Use of Laboratory Animals" (National Research Council, 1996). Rats were fed gamma irradiated rodent chow and tap water ad libitum.

The following implant compositions were tested: (a) short fiber DBM paste, prepared as described in Example 3; (b) short fiber DBM-calcium phosphate paste with carboxymethyl cellulose additive, prepared as described in Example 4; (c) short fiber DBM preformed cylindrical device, prepared as described in Example 5; (d) particulate DBM, prepared as described in Example 6; and (e) Grafton® DBM Putty. The particulate DBM and Grafton® DBM Putty served as controls.

Thirty-five (35) animals were randomly implanted with four different test articles, two in the thoracic musculature (pectoris major muscle) and two in the hind limbs (quadriceps). Each animal received an intraperitoneal (IP) injection of ketamine (100 mg/kg) and xylazine (10 mg/kg). Upon complete anesthetization, a small incision was made with a scalpel at the first implantation site, and the skin, subcutaneous tissue, and fascia were bisected with scissors. An intramuscular pouch was formed using pointed scissors to enter the desired muscle. The first cut was made in the same direction as the muscle fibers, and the scissors were spread to create a small pocket, which was held open while 0.1 ml of the test article was administered with forceps. Once the test article had solidified (at least 6 minutes), the muscle pocket was sutured closed. The surgery was then repeated at the remaining three implant sites. If necessary, an additional half dose of ketamine/xylazine was administered to maintain anesthetization sufficient to complete the implantation procedure.

Daily clinical observations were performed on each animal for seven days post-implantation. Biweekly clinical observations were performed thereafter.

The short fiber DBM pastes and short fiber DBM preformed cylindrical devices were retrieved four weeks following implantation. The short fiber DBM—calcium phosphate pastes were retrieved six weeks following implantation. The particulate DBM and Grafton® DBM Putty controls were retrieved at both four weeks and six weeks following implantation. Animals were euthanized by $CO_2$ overdose immediately prior to retrieval. Tissue collections were limited to the implant material and approximately 0.5 cm margins of skeletal muscle and/or connective tissue. Tissue specimens were fixed in 10% neutral buffered formalin for a minimum of 12 hours. Tissue specimens were bisected transversely at the implant midsection, routinely processed for paraffin embedding, cut onto glass slides, stained with hematoxylin and eosin, and coverslipped. If necessary, tissue specimens were additionally decalcified prior to histologic analysis.

Histologic analysis indicated that all short fiber DBM compositions showed bone formation and osteoblastic activity comparable to that of the control particulate DBM and Grafton® DBM Putty implants. The new bone formation and osteoblastic activity of the short fiber DBM compositions were significant, as evidence by the presence of new bone matrix containing osteocytes, osteoblasts, and bone marrow throughout the implants.

What is claimed is:

1. A demineralized bone matrix composition comprising:
   fibers of demineralized bone matrix consisting of fiber lengths between 250 μm to 2 mm and an aspect ratio of greater than about 4; and
   a biocompatible liquid in an amount to produce a coherent, formable mass.

2. The composition of claim 1, wherein the demineralized bone matrix fibers have an average thickness in the range from about 50 μm to about 250 μm.

3. The composition of claim 1, wherein the aspect ratio of said fibers is greater than about 10.

4. The composition of claim 1, wherein the aspect ratio of said fibers is in a range from about 10 to about 50.

5. The composition of claim 1, wherein the demineralized bone matrix fibers have an average width to average thickness ratio of less than about 5.

6. The composition of claim 1, wherein the biocompatible liquid is selected from the group consisting of water, saline, buffer solution, serum, bone marrow aspirant, blood, platelet-rich plasma, and mixtures thereof.

7. The composition of claim 1, further comprising particles of demineralized bone matrix having an aspect ratio of less than about 3.

8. The composition of claim 1, wherein the composition further comprises an osteoinductive additive.

9. The composition of claim 8, wherein the osteoinductive additive is selected from the group consisting of bone marrow aspirant, blood, blood products, synthetic and naturally-derived bone morphogenic proteins, growth factors, particulate demineralized bone matrix, and mixtures thereof.

10. The composition of claim 1, wherein the composition further comprises an osteoconductive additive.

11. The composition of claim 10, wherein the osteoconductive additive is selected from the group consisting of calcium phosphates, collagen, collagen-derivatives, calcium sulfate, particulate demineralized bone matrix, naturally-derived allogenic bone mineral, and naturally-derived autogenic bone mineral.

12. The composition of claim 1, wherein the composition further comprises an additive that modifies the handling characteristics of the composition.

13. The composition of claim 12, wherein the additive at least partially coats the demineralized bone fibers.

14. The composition of claim 12, wherein the additive is selected from the group consisting of gelatin, carboxymethyl cellulose, hydroxypropyl methylcellulose, methylcellulose, hydroxyethyl cellulose, cellulose derivatives, alginate, hyaluronic acid, sodium salts, polyvinyl pyrrolidones, polyvinyl alcohol, arabic gum, guar gum, xantham gum, chitosans, and poloxamers.

15. The composition of claim 1, wherein the relative amounts of demineralized bone matrix fibers and biocompatible liquid range from about 1:10 to about 10:1 wt/wt.

16. The composition of claim 1, wherein the relative amounts of demineralized bone matrix fibers and biocompatible liquid range from about 1:4 to about 4:1 wt/wt.

17. The composition of claim 1, wherein the relative amount of demineralized bone matrix fibers and biocompatible liquid is about 1:1 wt/wt.

18. The composition of claim 1, wherein the demineralized bone matrix fibers are obtained from cortical autogenic, cortical allogenic, cortical xenogeneic, cancellous autogenic, cancellous allogenic, cancellous xenogeneic, corticocancellous autogenic, corticocancellous allogenic, or corticocancellous xenogeneic bone.

19. The composition of claim 1, wherein the composition has a consistency such that it is injectable through an 18-gauge needle.

20. A demineralized bone matrix composition comprising:
   (a) a dry component comprising fibers of demineralized bone matrix consisting of fiber lengths between 250 μm to 2 mm and an aspect ratio of greater than about 4, wherein said demineralized bone matrix fibers are present in an amount greater than 40 wt % of said dry component, and
   (b) a biocompatible liquid in an amount to produce a coherent formable mass.

21. The composition of claim 20, wherein the demineralized bone matrix fibers have an average thickness in the range from about 50 μm to about 250 μm.

22. The composition of claim 20, wherein the demineralized bone matrix fibers have an aspect ratio greater than about 10.

23. The composition of claim 20, wherein the demineralized bone matrix fibers have an average width to average thickness ratio of less than about 5.

24. The composition of claim 20, further comprising an additive selected from the group consisting of osteoconductive additives, osteoinductive additives, and additives that modify the handling characteristics of the composition.

25. A demineralized bone matrix fiber composition, comprising:
   a collection of fibers of demineralized bone matrix of which at least 25 wt % between 250 μm to 2 mm and an aspect ratio of greater than about 4.

26. The composition of claim 25, wherein at least 50 wt % of the demineralized bone matrix fibers have between 250 μm to 2 mm and an aspect ratio of greater than about 4.

27. The composition of claim 25, wherein at least about 75 wt % of the demineralized bone matrix fibers have fiber lengths between 250 μm to 2 mm and an aspect ratio of greater than about 4.

28. The composition of claim 25, wherein the demineralized bone matrix fibers have an average thickness in the range from about 50 μm to about 250 μm.

29. The composition of claim 25, wherein the demineralized bone matrix fibers have an average width to average thickness ratio of less than about 5.

30. The composition of claim 25, further comprising an additive selected from the group consisting of osteoinductive additives, osteoconductive additives, and additives that modify the handling characteristics of the composition.

31. A preformed demineralized bone matrix article having a predetermined shape, said article comprising:
   fibers of demineralized bone matrix having consisting of fiber lengths between 250 μm to 2 mm and an aspect ratio of greater than about 4; and
   a biocompatible liquid in an amount to produce a coherent, formable mass.

32. The article of claim 31, wherein said article has a density in the range of about 0.3 g/cc to about 0.7 g/cc.

33. The article of claim 31, wherein said article has a compression strength greater than about 10 MPa.

34. A method for making a demineralized bone matrix composition, comprising:
   combining fibers of demineralized bone matrix, having consisting of fiber lengths between 250 μm to 2 mm and an aspect ratio of greater than about 4, and an amount of a biocompatible liquid to produce a coherent, formable mass.

35. A method of making a preformed demineralized bone matrix article having a predetermined shape comprising:
   combining fibers of demineralized bone matrix having consisting of fiber lengths between 250 μm to 2 mm and an aspect ratio of greater than about 4, and an amount of a biocompatible liquid to produce a coherent, formable mass;
   forming the mass into a preformed article having the predetermined shape; and
   drying the preformed article.

36. The method of claim 35, wherein the preformed article is lyophilized.

37. The method of claim 36, wherein the preformed article has a density of about 0.3 g/cc.

38. The method of claim 35, wherein the preformed article is oven dried.

39. The method of claim 38, wherein the preformed article has a density of about 0.7 g/cc.

* * * * *

UNITED STATES PATENT AND TRADEMARK OFFICE
CERTIFICATE OF CORRECTION

| | |
|---|---|
| PATENT NO. | : 7,582,309 B2 |
| APPLICATION NO. | : 10/298112 |
| DATED | : September 1, 2009 |
| INVENTOR(S) | : Rosenberg et al. |

It is certified that error appears in the above-identified patent and that said Letters Patent is hereby corrected as shown below:

On the cover page,

[*] Notice: Subject to any disclaimer, the term of this patent is extended or adjusted under 35 USC 154(b) by 56 days Delete the phrase "by 56 days" and insert -- by 509 days --

Signed and Sealed this

Thirty-first Day of August, 2010

David J. Kappos
*Director of the United States Patent and Trademark Office*

UNITED STATES PATENT AND TRADEMARK OFFICE
CERTIFICATE OF CORRECTION

PATENT NO. : 7,582,309 B2
APPLICATION NO. : 10/298112
DATED : September 1, 2009
INVENTOR(S) : Aron D. Rosenberg et al.

It is certified that error appears in the above-identified patent and that said Letters Patent is hereby corrected as shown below:

In the Specification

Column 4, Line 41, replace "noncancelous" with --noncancellous--.

Column 5, Line 6, replace "solubalized" with --solubilized--.

Column 6, Line 41, replace "Theological" with --rheological--.

Column 10, Line 32, replace "Average fiber length" with --The fiber length--.

Column 11, Line 28, replace "($Na_2HPO_4.7H_2O$)" with --($Na_2HPO_4 \cdot 7H_2O$)--;

Line 31, replace "($Na_4P_2O_7.10H_2O$)" with --($Na_4P_2O_7 \cdot 10H_2O$)--;

Line 33, replace "($Ca(NO_3)_2.4H_2O$)" with --($Ca(NO_3)_2 \cdot 4H_2O$)--;

Line 35, replace "($MgCl_2.6H_2O$)" with --($MgCl_2 \cdot 6H_2O$)--.

Column 12, Line 26, replace "sagital saw" with --sagittal saw--.

In the Claims

Column 15, Claim 25, Line 11, replace "at least 25 wt % between 250 µm" with
--at least 25 wt % have fiber lengths between 250 µm--;

Claim 26, Line 14, replace "have between" with --have fiber lengths between--;

Claim 31, Line 32, replace "matrix having consisting" with --matrix consisting--.

Column 16, Claim 34, Lines 9-10, replace "matrix, having consisting" with --matrix, consisting--;

Claim 34, Lines 9-11, replace "bone matrix, consisting of fiber lengths between 250 µm to 2 mm and an aspect ratio of greater than about 4, and an amount"

with

--bone matrix consisting of fiber lengths between 250 µm to 2 mm and an aspect ratio of greater than about 4 and an amount--;

Claim 35, Lines 16-17, replace "matrix having consisting" with --matrix consisting--.

Signed and Sealed this
Twenty-third Day of July, 2013

Teresa Stanek Rea
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 7,582,309 B2 | Page 1 of 1 |
| APPLICATION NO. | : 10/298112 | |
| DATED | : September 1, 2009 | |
| INVENTOR(S) | : Aron D. Rosenberg | |

It is certified that error appears in the above-identified patent and that said Letters Patent is hereby corrected as shown below:

ON THE TITLE PAGE: ITEM 73 REPLACE

"Boston, MA" with --Cambridge, MA--.

Signed and Sealed this

Eleventh Day of March, 2014

Michelle K. Lee
*Deputy Director of the United States Patent and Trademark Office*